United States Patent
Srivastava et al.

(10) Patent No.: US 6,303,764 B1
(45) Date of Patent: Oct. 16, 2001

(54) SYNTHESIS OF 4,7-DIALKYL CHROMOGENIC GLYCOSIDES OF N-ACETYLNEURAMINIC ACIDS

(75) Inventors: Om Srivastava; Geeta Srivastava; Minghui Du; Ole Hindsgaul; David R. Bundle, all of Edmonton (CA); Avraham Liav, Denver, CO (US)

(73) Assignees: Zymetx, Inc., Oklahoma City, OK (US); Palladin Opportunity Fund, LLC; Halifex Fund, L.P., both of Maplewood, NJ (US)

( * ) Notice: Subject to any disclaimer, the term of this patent is extended or adjusted under 35 U.S.C. 154(b) by 0 days.

(21) Appl. No.: 09/406,024

(22) Filed: Sep. 24, 1999

Related U.S. Application Data (60) Provisional application No. 60/101,928, filed on Sep. 24, 1998.

(51) Int. Cl.[7] ........................................ G07G 3/00
(52) U.S. Cl. ..................... 536/4.1; 536/4.1; 536/17.2; 536/17.3; 536/17.4; 536/17.9; 536/18.4; 536/18.5
(58) Field of Search ................. 536/4.1, 17.2, 536/17.3, 17.4, 17.9, 18.4, 18.5

(56) References Cited

U.S. PATENT DOCUMENTS

| | | | |
|---|---|---|---|
| 3,950,322 | 4/1976 | Thomas et al. | 260/210 R |
| 4,632,901 | 12/1986 | Valkirs et al. | 435/5 |
| 4,772,553 | 9/1988 | Fujii et al. | 435/13 |
| 4,810,636 | 3/1989 | Corey | 435/14 |
| 4,877,727 | 10/1989 | Miike et al. | 435/24 |
| 5,081,017 | 1/1992 | Longoria | 435/30 |
| 5,252,458 | 10/1993 | Liav et al. | 435/5 |
| 5,489,675 | 2/1996 | Sabesan | 536/17.2 |
| 5,556,963 | 9/1996 | Liav et al. | 536/55.3 |
| 5,663,055 | 9/1997 | Turner et al. | 536/55.3 |
| 5,719,020 | 2/1998 | Liav et al. | 435/5 |
| 5,766,841 * | 6/1998 | Liav et al. | 435/6 |

FOREIGN PATENT DOCUMENTS

| | | |
|---|---|---|
| 01290695 * | 11/1989 | (JP) . |
| WO 91/09972 | 7/1991 | (WO) . |
| WO 91/16320 | 10/1991 | (WO) . |
| WO 92/06691 | 4/1992 | (WO) . |
| 98/013372 * | 4/1998 | (WO) . |

OTHER PUBLICATIONS

Liav et al., "Synthesis of bromoindolyl 4,7-di-O-methyl-Neu5Ac: specificity toward influenza A and B viruses", Carb. Res., vol. 317(1–4): 198–203, Apr. 1999.*

Reinhard et al., "Regioselective Acetylations of Sialic Acid alpha–Ketosides", Liebigs Ann. Chem., 193–203, 1994.*

Kuboki et al., "A Facile Access to Aryl alpha–Sialosides: the combination of a volatile amine base and acetonitrile in glycosidation of sialosyl chlorides", Synlett, 479–482, May 1998.*

Vasella et al., "Synthesis of the 6–C–methyl and 6–C–(hydroxymethyl) analogues of N–acetylneuraminic acid and of N–acetyl-2,3–didehydro–2–deoxyneuraminic acid", Helv. Chim. Acta, vol. 73: 1742–1763, 1990.*

Pachucki, "Early Detection of Influenza Virus By Using a Fluorometric Assay of Infected Tissue Culture", *J. of Clinical Microbiology*, vol. 26, No. 12 (Dec. 1988) pp. 2664–2666.

Yolken et al., "Fluorometric Assay for Measurement of Viral Neuraminidase—Application to the Rapid Detection of Influenza Virus in Nasal Wash Specimens", *J. of Infectious Diseases*, vol. 142, No. 4, (Oct. 1980) pp. 516–523.

Zbiral et al., "Synthesis of the 4–Methylumbelliferyl 2α–Glycosides of 7–Epi, 8–Epi–, and 7,8–Bis(epi)–N–acetylneuraminic Acids, as well as of 7–Deoxy–, 8–Deoxy,9–Deoxy, and 4,7–Dideoxy–N–acetylneuraminic Acids and Their Behaviour Towards Sialidase from Vibrio cholerae", *Liebigs, Ann. Chem.* (1989) pp. 519–526.

Zbiral et al., Structural Transformations of N–Acetylneuraminic Acid, VII. Synthesis of 7–,8–, 9–Desoxy– and 4,7–Didesoxyneuraminic Acid, *Monatshefte fur Chemie*, vol. 119 (1988) pp. 127–141.

Kim et al., "Enzymes in Carbohydrate Synthesis: N–Acetylneuraminic Acid Aldolase Catalyzed Reactions and Preparation of N–Acetyl–2–deoxy–D–neuraminic Acid Derivatives" *J. Am. Chem. Soc.*, vol. 110 (1988), pp. 6481–6486.

Kiyotani et al., "Enzymological Characteristics of Avian Influenza A Virus Neuraminidase" *Microbiol. Immunol.*, vol. 31, No. 11 (1987) pp. 1131–1135.

Kiyotani et al., Enzymological Heterogeneity of Influenza B Virus Neuraminidase Demonstrated by the Fluorometric Assay Method, *Zbl. Bakt. Hyg.*, vol. (A260) (1985) pp. 273–285.

Kiyotani et al., "Fluorometric Measurement of Neuraminidase Activity of Influenza Viruses", *Hiroshima J. of Medical Sciences*, vol. 33, No. 2, pp. 287–292.

(List continued on next page.)

*Primary Examiner*—Ralph Gitomer
*Assistant Examiner*—D Khare (57) ABSTRACT

The present invention provides an improved method of preparing a 4,7-di-O-alkyl chromogenic ketoside of N-acetylneuraminic acid (Neu5Ac) for use in detecting influenza virus types A and B. The ketosides are substrates that are selectively cleaved by a neuraminidase on influenza virus, but not be neuraminidases found on other viruses or on bacteria. The synthesis is efficient and provides large quantities of the ketoside for commercial development. The synthesis includes a step of alkylating the 4- and 7-hydroxyl groups of a protected alkyl ester alkyl ketoside derivative of Neu5Ac by a process that comprises contacting the derivative with a composition comprising an alkyl halide to form a 4,7-di-O-alkyl protected alkyl ester alkyl ketoside derivative of Neu5Ac. The synthesis alternatively includes protecting the 8- and 9-hydroxyl groups of an alkyl ester alkyl ketoside derivative of Neu5Ac by forming an 8,9-epoxide protected alkyl ester alkyl ketoside derivative of Neu5Ac.

30 Claims, 2 Drawing Sheets

OTHER PUBLICATIONS

Yolken, "Enzyme Immunoassays for the Detection of Infectious Antigens in Body Fluids: Current Limitations and Future Prospects", *Review of Infectious Diseases*, vol. 4, No. 1 (1982) pp. 35–68.

Yolken, "Enzymic Analysis for Rapid Detection of Microbial Infection in Human Body Fluids: An Overview", *Clinical Chem.*, vol. 27, No. 9 (1981), pp. 1490–1498.

Myers et al. "The Synthesis of 4–Methylumbelliferyl α–Ketoside of N–Acetylneuraminic Acid and Its Use in a Fluorometric Assay for Neuraminidase", *Analytical Biochem.*, vol. 101, (1980), pp. 166–174.

Santer, "A Rapid Assay for Neuraminidase—The Detection of Two Differences in Activity Associated With Virus Transformation", *Biochimica et Biophysica Acta*, vol. 523, (1978) pp. 435–442.

Beau et al., "Metabolism of 4–O–Methyl–N–acetyl-neuraminic Acid a Synthetic Sialic Acid", *Eur. J. Biochem.*, vol. 106, (1980), pp. 4279–4283.

Gross et al. Interaction of N–Acetyl–4–epi–D–neuraminic Acid with Key Enzymes of Sialic Acid Metabolism, *Biochemistry*, vol. 27, (1988) pp. 4279–4283.

Hagedorn et al., "Synthesis and Biological Properties of N–Acetyl–4–deoxy–D–neuraminic Acid" *Helvetica Chimica Acta*, vol. 69 (1986) pp. 2127–2133.

Gross et al., "N–Acetyl–4–deoxy–D–neuraminic Acid is Activated and Transferred on to Asialoglycoprotein", *Glycoconjugate*, (1984), 4:145–156.

Baumberger et al., "Synthesis of N–Acetyl–4–deoxyneuraminic Acid", *Helvetica Chemica Acta*, vol. 69 (1986).

Baumberger et al., "4–Methylumbelliferyl 5–Acetamido–3, 4,5–trideoxy–x–D–manno–2 nonulopyranosidonic Acid: Synthesis and Resistance to Bacterial Sialidases", *Helvetica Chimica Acta*, vol. 69 (1986) pp. 1927–1935.

Beau, et al., *Chemical Abstracts*, vol. 93, No. 5, Aug. 4, 1980 Columbus, Ohio, p. 394, col. 2.

Takei et al, "Enzymological Different characeristics Between Influenza A and B B Virus Neuraminidases", *Biological Abstracts*, vol. 82, No. 12.

Kiyotani et al., *Biological Abstracts*, vol. 81, No. 8, Issued 1986, Abstract No. 78292.

Kiyotani et al., *Biological Abstracts*, vol. 79, No. 3, Issued 1995, Abstract No. 27461.

Liav et al., "Synthesis of 6–O–mycoloyl and 6–O–corynomycoloyl–α,α–trehalose", *Carbohydrate Research*, 125 (1984) pp. 323–328.

Kuhn et al., Überführung Von 2–Amino–Desoxy–Hexosen in 3–Amino–3–Desoxy–Hexosen Und –Pentosen *Bd. 636*, pp. 164–173.

Beau et al., Synthese De L'Acide 4–O–Methyl–N–Acetylneuraminique. Partie I. Acetonation Du 3—Acetamido–3–Desoxy–D–glycero–D–galaco–Heptose Diethyldithioacetal, *Carbohydrate Research*, vol. 65 (1978) pp. 1–10.

Warner et al., "Synthesis of 2'–(4–Methylumbelliferyl)–α–D–Nacetylneuraminic Acid and Detection of Skin Fibroblas Neuraminidase in Normal Humans and in Sialidosis", *4–MU–NANA Neuraminidase*, vol. 18, No. 13, pp. 2783.

Rothermel, Jorg et al., "Phase–Transfer–Catalyzed Synthesis of Aryl α–Methylfluoran–6–YL Glycoside of N–Acetylneuranimic Acid, 2–Methyl–6–(5–Acetamido–3, 5–Dideoxy–α–D–glycero–D–galacto–Nonulopyranosyl–Onic Acid)Xanthene–9–Spiro–1'–Isobenzofuran–3'–One, a New Substrate for Neuraminidase Assay", *Carboyhydrate Research*, 196 (1990) pp. 29–40.

* cited by examiner

SYNTHESIS OF 4,7-DIALKYL CHROMOGENIC GLYCOSIDES OF N-ACETYLNEURAMINIC ACIDS

RELATED APPLICATIONS

This application is based on, and claims benefit of, U.S. Provisional Application Ser. No. 60/101,928 filed on Sep. 24, 1998.

FIELD OF THE INVENTION

This invention relates to an improved synthesis of derivatives of N-acetylneuraminic acid. The synthetic procedures represent improvements and enhancements that permit obtaining large quantities of the products suitable for commercial production. These derivatives of N-acetylneuraminic acid can be used as chromogenic substrates for the detection of viral neuraminidases.

BACKGROUND OF THE INVENTION

Viral infections are a principal cause of illness due to communicable diseases that affect the public at large. Of these, influenza viruses, including types A and B, are a significant factor responsible for causing respiratory symptoms as well as systemic malaise; other respiratory viruses include parainfluenza 1, 2, 3, and 4, respiratory syncytial virus, and adenovirus. The influenza viruses undergo rapid mutation of strains, producing pathogens with varying degrees of virulence and severity of symptoms. Recently, influenza infection has been as high as the fifth leading cause of death from acute respiratory disease in the United States (Morbidity and Mortality Weekly Report, 36 (1987) 2).

For this reason it is important to have available ways of diagnosing the presence of an influenza infection, and of distinguishing it from related viral and bacterial infections. Particularly among infants, the elderly and those having compromised or deficient immune responses, early diagnosis of influenza can lead to appropriate symptomatic treatment to minimize the risk of morbidity.

Diagnosis of viral infection, such as infection by influenza virus, may be carried out by detecting the presence of unique moieties characteristic of the virus. Virus particles typically carry distinctive antigenic components on the exterior of the virion which may be detected by specific ligand-antiligand interactions, in particular by the use of an antibody specific for a viral epitope. Such interactions rely on the law of mass action, and for this reason may have limited sensitivity. Many virus particles additionally carry specific enzymatic activities on the virion particle. Influenza virus is an example of such virus, endowed with a virus-specific neuraminidase activity as an integral part of the virion which is exposed to the environment. Utilization of the enzymatic activity in such cases offers the potential for increasing the sensitivity of a detection method.

N-acetylneuraminic acid (sialic acid, Neu5Ac), whose structure is shown below with atoms numbered,

[1]

is the terminal saccharide residue of many complex carbohydrate side chains of cell surface glycoproteins. In this structure the C2 position is the anomeric carbon, which is characterized by being part of a hemiketal group, or the 2-ketoside moiety. The glycosidic linkage bonding Neu5Ac with the penultimate saccharide is the substrate of the neuraminidase activity of the influenza virion. The neuraminidase hydrolyzes the linkage, thereby cleaving Neu5Ac from the penultimate saccharide. Consequently, suitable synthetic substrates may be derivatives of Neu5Ac in 2-ketoside linkage with a detectable moiety. The moiety then provides a product, when the substrate is acted upon by the viral neuraminidase activity, that signals the presence and amount of influenza virus particles in a sample. Since the viral enzyme cleaves the substrate catalytically, the sensitivity of detecting the presence of the enzyme is greatly enhanced. For this reason the overall sensitivity of detection may be comparable to, and may even be improved over, that provided by antibody binding assays.

One method for detecting the presence of a virus through the reaction of an enzyme with a chromogenic substrate for the enzyme is described in U.S. Pat. No. 5,252,458, which is incorporated herein by reference. An assay for the direct measurement of influenza neuraminidase was developed by Yolken et al. (J. Infectious Diseases 142 (1980) 516–523). Yolken et al. used the 4-methylumbelliferyl-2-ketoside of Neu5Ac as a fluorescent substrate to measure neuraminidase activity in preparations containing small quantities of cultivated virus as well as in some nasal wash specimens from human volunteers infected with the influenza virus. Yolken et al. suggested that "successful development of influenza neuraminidase might thus provide for a practical means of influenza diagnosis that is sufficiently rapid to allow for the institution of appropriate preventive and therapeutic interventions." According to Yolken et al., colorimetric assays were insufficiently sensitive for clinical applications, suggesting instead that fluorimetric assays for influenza neuraminidase might be suitable for detecting the virus in clinical samples.

Pachucki et al. (J. Clinical Microbiology 26 (1988) 2664–2666) tested the 4-methylumbelliferyl-2-ketoside of Neu5Ac on clinical specimens collected from influenza patients. Due to its low sensitivity, the assay was not useful in detecting neuraminidase in clinical specimens. The assay did, however, identify 91% of virus-positive isolates 25 hours after inoculation of tissue cultures.

The use of modified Neu5Ac substrates can increase the specificity of the neuraminidase assay. In sialic acids, the C4 position has been reported to play an important role in enzyme-substrate interactions. Further, since it is known that salivary bacterial enzymes exhibit neuraminidase activity (Varki et al., J. Biol. Chem. 258 (1983) 12465–12471), it is essential to avoid these undesired enzymatic activities. It has, for example, been shown that ketosides of 4-methoxy-Neu5Ac are resistant towards certain bacterial sialidases (Beau et al., Eur. J. Biochem. 106 (1980) 531–540).

Although modification of the 4-position of Neu5Ac's provides specificity between certain viral and certain bacterial neuraminidase activities, it is still desirable to obtain substrates which provide enhanced specificity between the various viral neuraminidase reactivities while maintaining the specificity between viral and bacterial neuraminidase activities. Such substrates allow, for example, high specificity for particular types of neuraminidase-containing viruses and allow better and more directed treatment regimes. Use of specific substrates thus allows for more accurate surveillance of viral infections and more focused medical intervention as appropriate. U.S. Pat. No. 5,719,020, incorporated herein by reference, provides chromogenic and fluorogenic 4,7-disubstituted N-acetylneuraminic acid substrates for viral neuraminidase activities. These derivatives provide further specificity or differentiation between the various viral neuraminidase activities while maintaining the specificity between viral and bacterial neuraminidase activities. In particular, in U.S. Pat. No. 5,719,020 it is shown that the 4,7-modified Neu5Ac chromogenic substrates disclosed therein distinguish between influenza type A and B viruses, on the one hand, and neuraminidases from other viral and bacterial pathogens, on the other. A chromogenic derivative of 4-O-methyl Neu5Ac, however, develops color when exposed to parainfluenza virus types 1 and 2, and mumps, in addition to influenza types A and B.

The synthetic procedures leading to the 4,7-disubstituted chromogenic Neu5Ac ketoside derivatives disclosed in U.S. Pat. No. 5,719,020 have certain difficulties associated with them. These include the provision of synthetic routes involving a large number of distinct chemical reactions. These require an excessive number of unit operations, leading to the need for many reagents, solvents, pieces of laboratory apparatus, and for extended time to obtain the product. Certain reactions disclosed in U.S. Pat. No. 5,719,020 involve the use of hazardous reagents or solvents. A number of additional steps involve chromatography with its attendant high consumption of solvents and dilution of the desired products. Additionally, many of the synthetic steps disclosed in U.S. Pat. No. 5,719,020 provide very poor yields. All these factors lead to considerable difficulties and disadvantages related to implementation of commercial scale preparations of 4,7-disubstituted chromogenic derivatives of Neu5Ac. As a result, it is costly and inefficient to prepare these substances on a scale suitable for commercial development.

The present invention addresses these deficiencies. As set forth in detail herein, the number of synthetic steps and attendant number of unit operations is minimized. The use of chromatographic separations likewise is minimized. Additionally, the synthetic reactions have been optimized and the recovery procedures enhanced to provide high step yields and thereby high overall yields for the final products that are unexpected by the present state of knowledge in the field. The resulting improvements permit economical preparation of viral neuraminidase substrates on the scale of kilograms for commercial sale.

SUMMARY OF THE INVENTION

The present invention provides a method of preparing a 4,7-di-O-alkyl chromogenic ketoside of N-acetylneuraminic acid (Neu5Ac) that includes sequential steps of:

(a) alkylating Neu5Ac on the C1 carboxyl and C2 (anomeric) hydroxyl to provide an alkyl ester alkyl ketoside derivative of Neu5Ac;

(b) protecting the 8- and 9-hydroxyl groups of the alkyl ester alkyl ketoside derivative of Neu5Ac to form a protected alkyl ester alkyl ketoside derivative of Neu5Ac;

(c) alkylating the 4- and 7- hydroxyl groups of the protected alkyl ester alkyl ketoside derivative of Neu5Ac with an alkyl halide to form a 4,7-di-O-alkyl protected alkyl ester alkyl ketoside derivative of Neu5Ac;

(d) selectively deprotecting the 8- and 9-hydroxyl groups and dealkylating the 2-hydroxyl group of the ketoside product obtained in step (c) and derivatizing the resulting 2-, 8-, and 9-hydroxyl groups;

(e) activating the anomeric carbon of the product obtained in step (d) to form a 4,7-di-O-alkyl alkyl ester derivative of Neu5Ac, derivatized at the 8- and 9-hydroxyls, and activated at the anomeric carbon;

(f) contacting the product obtained in step (e) with a suspension that includes a derivative of a chromogenic moiety in a solvent to form a chromogenic ketoside of a 4,7-di-O-alkyl alkyl ester derivative of Neu5Ac, derivatized at the 8- and 9-hydroxyls; and (g) obtaining a 4,7-di-O-alkyl chromogenic ketoside of Neu5Ac from the derivatized chromogenic ketoside obtained in step (f).

In a preferred embodiment of this method, protection of the 8- and 9-hydroxyl groups described in step (b) involves forming a ketal. In a further preferred embodiment of this method, forming the ketal is done in the presence of an acid catalyst chosen from the group consisting of p-toluenesulfonic acid, a salt of p-toluenesulfonic acid, $ZnCl_2$, and $FeCl_3$. In an additional preferred embodiment of this method, protecting the 8- and 9-hydroxyl groups described in step (b) includes dehydration to form an 8,9-epoxide.

The invention additionally provides a method of preparing a 4,7-di-O-alkyl chromogenic ketoside of Neu5Ac that includes sequential steps of:

(a) alkylating Neu5Ac on the C1 carboxyl and C2 hydroxyl to provide an alkyl ester alkyl ketoside derivative of Neu5Ac;

(b) protecting the 8- and 9-hydroxyl groups of the alkyl ester alkyl ketoside derivative of Neu5Ac by forming an 8,9-epoxide protected alkyl ester alkyl ketoside derivative of Neu5Ac;

(c) alkylating the 4- and 7-hydroxyl groups of the epoxide protected alkyl ester alkyl ketoside derivative of Neu5Ac to form a 4,7-di-O-alkyl epoxide protected alkyl ester alkyl ketoside derivative of Neu5Ac;

(d) selectively deprotecting the 8- and 9-hydroxyl groups and dealkylating the 2-hydroxyl group of the ketoside product obtained in step (c) and derivatizing the resulting 2-, 8-, and 9-hydroxyl groups;

(e) activating the anomeric carbon of the product obtained in step (d) to form a 4,7-di-O-alkyl alkyl ester derivative of Neu5Ac, derivatized at the 8- and 9-hydroxyls, and activated at the anomeric carbon;

(f) contacting the product obtained in step (e) with a suspension that includes a derivative of a chromogenic moiety in a solvent to form a chromogenic ketoside of a 4,7-di-O-alkyl alkyl ester derivative of Neu5Ac, derivatized at the 8- and 9-hydroxyls; and (g) obtaining a 4,7-di-O-alkyl chromogenic ketoside of Neu5Ac from the derivatized chromogenic ketoside obtained in step (f).

In a further preferred embodiment of this method, the alkylating described in step (c) includes contacting the derivative with a composition that includes an alkyl halide to form a 4,7-di-O-alkyl epoxide protected alkyl ester alkyl ketoside derivative of Neu5Ac.

In preferred embodiments of both methods described in the preceding paragraphs, the alkyl group on the C1 carboxyl and the alkyl group on the anomeric hydroxyl of the ketoside derivative of Neu5Ac described in step (a) are the same or different and may be methyl, ethyl, propyl, isopropyl, or normal or branched butyl. In more preferred embodiments of these methods, both alkyl groups are methyl.

In further preferred embodiments of the methods described above, the alkylation performed in steps (c) of the methods uses methyl iodide in the presence of either silver oxide or a mixture of barium oxide and barium hydroxide. In yet an additional embodiment of these methods, the anomeric (C2) carbon is activated in steps (e) of the methods by halogenating it, and more preferably by chlorinating it.

In still additional embodiments of these methods, the suspension described in steps (f) of the methods further includes a base. In preferred embodiments the base may be sodium hydroxide, an alkali metal alkoxide, or a mixture of barium oxide and barium hydroxide. In more preferred embodiments, the base is an alkali metal alkoxide or a mixture of barium oxide and barium hydroxide.

In additional embodiments of both methods the chromogenic moiety is chosen from among 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl, a moiety that becomes phosphorescent upon being cleaved from the ketoside, and a moiety that becomes chemiluminescent upon being cleaved from the ketoside. In more preferred embodiments of these methods, the chromogenic moiety is 5-bromo-3-indolyl.

The invention additionally discloses a method of preparing a 4,7-di-O-methyl chromogenic ketoside of N-acetylneuraminic acid (Neu5Ac) that includes sequential steps of:
(a) contacting Neu5Ac with a composition that includes methanol and the protonated form of a cation exchange resin to methylate the C1 carboxyl group and the C2 hydroxyl group, forming a methyl ester methyl ketoside of Neu5Ac;
(b) contacting the methylated ester ketoside of Neu5Ac provided in step (a) with a composition that includes acetone and p-toluenesulfonic acid, to form a 8,9-isopropylidene methyl ester methyl ketoside of Neu5Ac;
(c) contacting the 8,9-isopropylidene methylated ester ketoside of Neu5Ac provided in step (b) with a composition containing methyl iodide and a mixture of barium oxide and barium hydroxide to form a 4,7-di-O-methyl 8,9-isopropylidene methyl ester methyl ketoside of Neu5Ac;
(d) selectively removing the 8,9-isopropylidene and C2 methyl groups from the ketoside product obtained in step (c) and acetylating the resulting anomeric, 8- and 9-hydroxyl groups;
(e) activating the anomeric carbon of the product obtained in step (d) by converting the acetate to chloride;
(f) contacting the activated chloride product provided in step (e) with a suspension containing a derivative of 5-bromo-3-indolol and potassium tert-butoxide in a solvent to form a chromogenic ketoside of a 4,7-di-O-methyl methyl ester of Neu5Ac, acetylated at the 8- and 9-hydroxyls; and
(g) deblocking the acetyl groups at the 8- and 9-hydroxyl groups and the methyl ester from the chromogenic ketoside of Neu5Ac obtained in step (f), to form the 4,7-di-O-methyl chromogenic ketoside of Neu5Ac.

The present invention also provides a method of preparing a 4,7-di-O-methyl chromogenic ketoside of N-acetylneuraminic acid (Neu5Ac) that includes sequential steps of:
(a) contacting Neu5Ac with a composition that includes methanol and the protonated form of a cation exchange resin to methylate the C1 carboxyl group and the C2 hydroxyl group, forming a methyl ester methyl ketoside of Neu5Ac;
(b) contacting the methylated ester ketoside of Neu5Ac provided in step (a) with
　(i) a composition containing the acid chloride of an organic sulfonic acid, and
　(ii) treating the result obtained in step (b) (i) with a composition containing sodium methoxide and methanol, providing an 8,9-epoxide methyl ester methyl ketoside of Neu5Ac;
(c) methylating the 4- and 7-hydroxyl groups of the 8,9-epoxide methylated ester ketoside of Neu5Ac provided in step (b) by either
　(i) contacting the epoxide ketoside with a composition containing methyl iodide and silver oxide,
　(ii) contacting the epoxide ketoside with a composition containing dimethylsulfate and sodium hydride, or
　(iii) a sequential combination of step (c)(i) and step (c)(ii), providing a 4,7-di-O-methyl 8,9-epoxide methylated ester ketoside of Neu5Ac;
(d) selectively removing the 8,9-epoxide and C2 methyl groups from the ketoside product obtained in step (c) and acetylating the resulting anomeric, 8- and 9-hydroxyl groups;
(e) activating the anomeric carbon of the product obtained in step (d) by converting the acetate to chloride;
(f) contacting the activated chloride product provided in step (e) with a suspension containing a derivative of 5-bromo-3-indolol and potassium tert-butoxide in a solvent to form a chromogenic ketoside of a 4,7-di-O-methyl methyl ester of Neu5Ac, acetylated at the 8- and 9-hydroxyls; and
(g) deblocking the acetyl groups at the 8- and 9-hydroxyl groups and the methyl ester from the chromogenic ketoside of Neu5Ac obtained in step (f), to form the 4,7-di-O-methyl chromogenic ketoside of Neu5Ac.

DETAILED DESCRIPTION OF THE INVENTION

This invention describes improved synthetic processes for the preparation of 4,7-dialkylated chromogenic derivatives of Neu5Ac in quantities suitable for commercial development. In general, the chromogenic substrates, which contain the chromogenic moiety in ketosidic linkage with the Neu5Ac derivative, interact poorly with light so that they neither absorb nor emit light to a significant extent. However, when acted upon by the viral neuraminidase, the chromogenic substrate liberates the chromogenic moiety as a free compound, no longer bound in ketosidic linkage to the derivatized Neu5Ac. The free chromogenic moiety in its most general sense, interacts with light to a significant extent either absorbing light at a particular wavelength (serving as a chromophore) or emitting light of a particular wavelength from an excited state. The excited state may arise from exposure to appropriate exciting radiation, or from chemically-induced excitation. These give rise respectively to luminescence, which comprises fluorescence and phosphorescence, and chemiluminescence. As used herein and for purposes of providing a convenient shorthand reference, the term "chromogenic" describes moieties that may be detectable by any of these processes, namely, absorption of light of a characteristic wavelength, and emission of light at a characteristic wavelength by fluorescence, phosphorescence, or chemiluminescence.

The substrates that are synthesized by the processes disclosed in this invention are characterized generally by the formula wherein $R_1$ and $R_2$ generally are the same or different and may be methyl, ethyl, propyl, isopropyl, and normal or branched butyl. The 2-ketoside is linked to the chromogenic moiety Y in the β-anomeric configuration. In general Y may be any chromogenic moiety such that, when cleaved by the action of a neuraminidase, the alcohol HOY is chromogenic within the meaning of this disclosure. Examples of chromophoric and fluorescent chromogenic moieties designated by Y include 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl. Additionally, Y may generally be a radical such that the hydrolysis product HOY exhibits phosphorescence or chemiluminescence.

The chromogenic ketosides provided by the improved synthetic strategies disclosed in this invention include 4-methylumbelliferyl 4,7-di-O-alkyl Neu5Ac ketoside, 3-cyanoumbelliferyl 4,7-di-O-alkyl Neu5Ac ketoside, 2-nitrophenyl 4,7-di-O-alkyl Neu5Ac ketoside, 4-nitrophenyl 4,7-di-O-alkyl Neu5Ac ketoside, 3-resorufin 4,7-di-O-alkyl Neu5Ac ketoside, 5-bromo-4-chloro-3-indolyl 4,7-di-O-alkyl Neu5Ac ketoside, 5-bromo-3-indolyl 4,7-di-O-alkyl Neu5Ac ketoside, 3-indolyl 4,7-di-O-alkyl Neu5Ac ketoside, nitrophenylazophenyl 4,7-di-O-alkyl Neu5Ac ketoside, nitrophenylazoresorcinyl 4,7-di-O-alkyl Neu5Ac ketoside, 3-methoxyphenyl 4,7-di-O-alkyl Neu5Ac ketoside, 3-dimethylaminophenyl 4,7-di-O-alkyl Neu5Ac ketoside, 4-chloro-1-naphthyl 4,7-di-O-alkyl Neu5Ac ketoside, and 6-bromo-2-naphthyl 4,7-di-O-alkyl Neu5Ac ketoside; and in addition a phosphorescent 4,7-di-O-alkyl Neu5Ac ketoside and a chemiluminescent 4,7-di-O-alkyl Neu5Ac ketoside.

Figure 1:
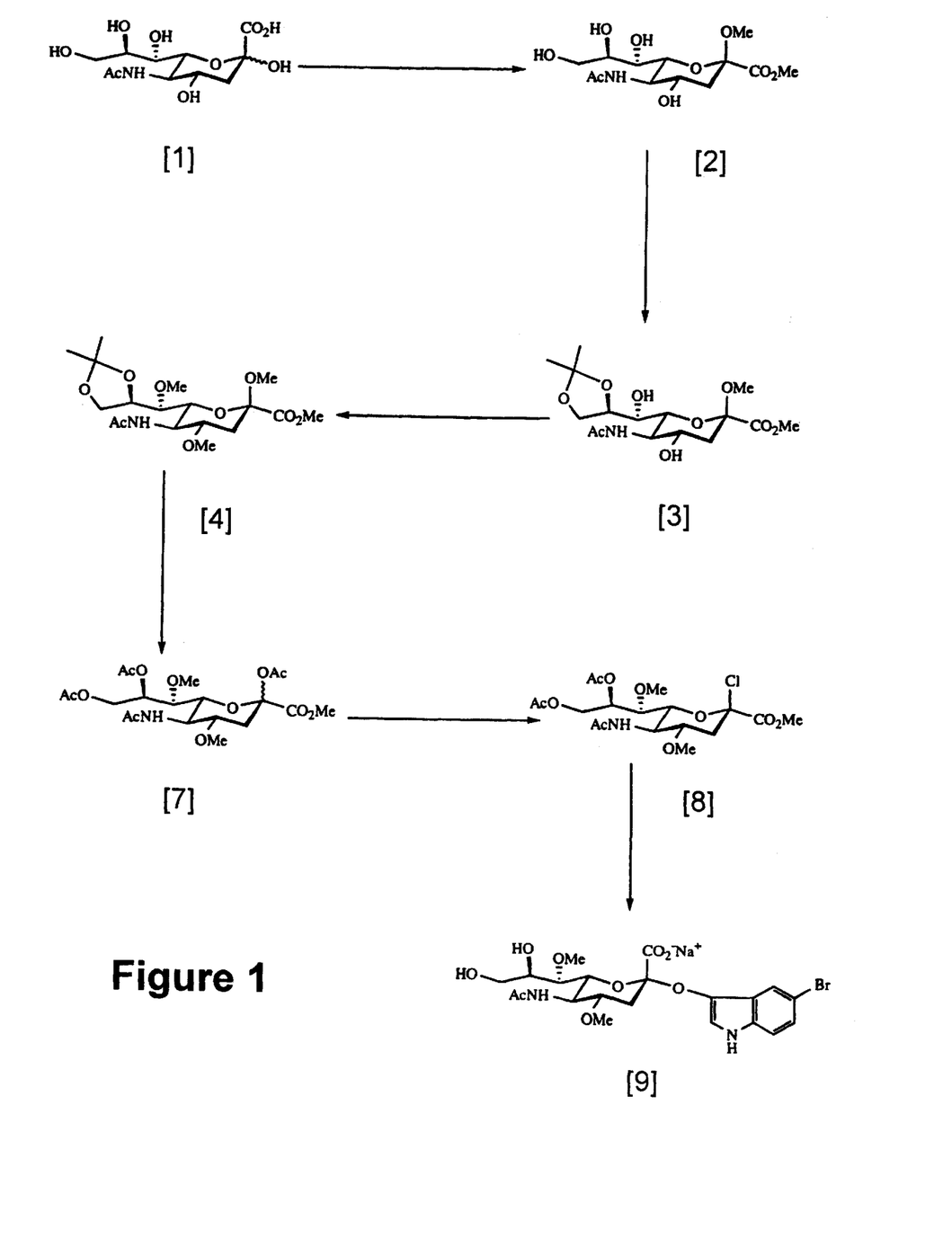
FIG. 1. Schematic diagram presenting a reaction scheme leading to the synthesis of 4,7-di-O-alkyl 5-bromo-3-indolyl ketoside of Neu5Ac via an 8,9-ketal protecting group.
Figure 2:
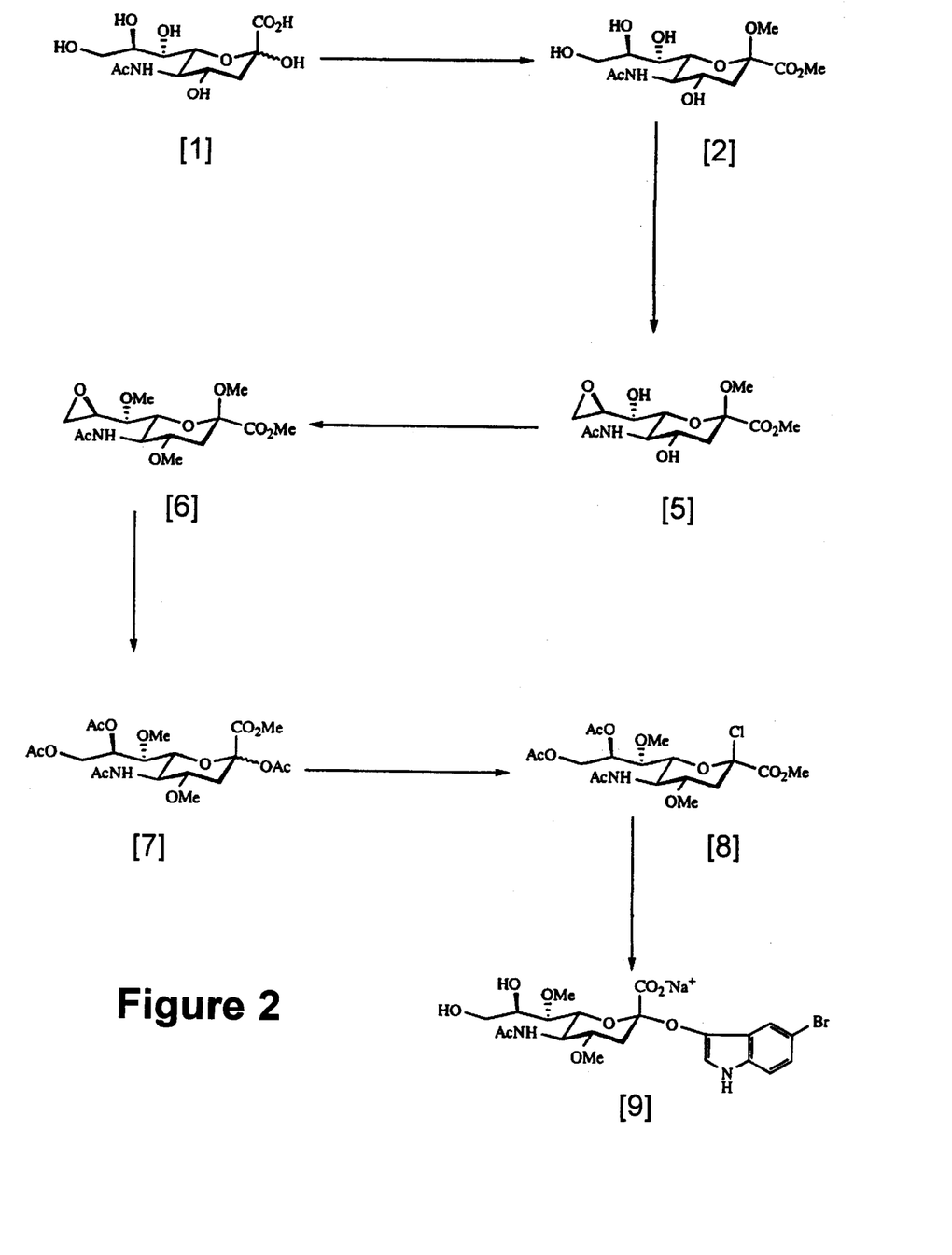
FIG. 2. Schematic diagram presenting a reaction scheme leading to the synthesis of 4,7-di-O-alkyl 5-bromo-3-indolyl ketoside of Neu5Ac via an 8,9-expoxide protecting group.

The synthesis disclosed herein improves on reactions and processes set forth in U.S. Pat. Nos. 5,556,963 and 5,719,020, whose disclosures are hereby incorporated by reference. The description of this invention provided below characterizes a preferred embodiment in which the alkyl group at the ester linkage and the alkyl ketoside group are both methyl. The starting material is Neu5Ac, which is available from MediHerb Inc. (4540 S. Navajo #1, Englewood Colo. 80110). Neu5Ac is first converted to a dimethyl derivative wherein the carboxyl of C1 and the anomeric hydroxyl on C2 are methylated simultaneously in a single reaction. Typically this can be effected by treatment with methanol under conditions of acid catalysis. A useful and effective acid catalyst is the protonated form of a strong acid cation exchange resin, such as Bio-Rad protonated resin Nafion™ (Hercules, Calif.). The result is a methyl ester methyl ketoside of Neu5Ac:

Crude yields range from about 90% to about 96%, providing a yield upon crystallization of about 65% for this step. Other well known cation exchange resins were tried but provided poor yields for this step. Furthermore, soluble strong acids such as HCl, sulfuric acid, trifluoroacetic acid and a sulfonic acid provided a product in which only the ester group was formed.

In the next step the 8,9- vicinal diol group is protected by a specific reaction. In a preferred embodiment this protection is afforded by preparation of an 8,9-isopropylidene derivative, the ketal provided by reaction with acetone under acid catalysis. Useful acid catalysts include p-toluenesulfonic acid, salts of p-toluenesulfonic acid such as pyridinium p-toluenesulfonate, and acidic salts such as $ZnCl_2$ and $FeCl_3$. A preferred acid catalyst for ketal formation is p-toluenesulfonic acid. This reaction is a single step protection of the 8,9 dihydroxy grouping, affording the ketal in essentially quantitative yield requiring no chromatography for purification. The result is an 8,9-isopropylidene Neu5Ac methyl ester methyl ketoside:

In an alternative embodiment, the protective grouping for the 8,9-diol involves formation of an epoxide. This is a two-step reaction in which the aryl- or alkyl-sulfonyl chloride derivatives the 9-hydroxyl group. This intermediate is then induced to cyclize by the addition of sodium methoxide, yielding an 8,9-epoxide derivative of the Neu5Ac methyl ester methyl ketoside:

Preferred acid chlorides include methanesulfonyl chloride, p-toluenesulfonyl chloride, and 2-mesitylenesulfonyl chloride. In this procedure, purification by silica gel chromatography is employed, providing a step yield of about 65%.

The next step generates a 4,7-dialkylated derivative of the protected and methylated Neu5Ac. U.S. Pat. No. 5,719,020 discloses that, generally a mixture of the 4-monoalkylated derivative and the 4,7-dialkylated derivative is obtained by the methods disclosed therein. It appears from an extensive discussion in the patent that the 7-hydroxyl is in a more sterically hindered environment than the 4-hydroxyl when the 8,9-dihydroxy grouping is protected by the isopropylidene substituent, and thereby is more difficult to alkylate successfully. In contrast, the procedures developed in the present invention provide the 4,7-dialkyl derivative in high yield. In general the alkyl groups at the 4- and 7-positions are the same or different, and may be methyl, ethyl, propyl, isopropyl, and normal or branched butyl. In a preferred embodiment of the invention, the synthetic reaction employed at this stage of the method provides the 4,7-di-O-methyl derivative.

The actual reaction procedures used for preparing the 4,7-di-O-alkylated derivative depend on the 8-, 9-protecting group used in the previous reaction step. When the 8,9-dihydroxy grouping is protected by the isopropylidene derivative, dialkylation may be achieved by reaction with an alkyl halide, preferably a higher halide such as bromide or iodide, in the presence of a basic substance. As noted above, the alkyl group may be methyl, ethyl, propyl, isopropyl, and normal or branched butyl. In a preferred embodiment of the method of the invention, the reagent employed in this reaction is methyl iodide, leading to the synthesis of the 4,7-di-O-methyl derivative. An excess of methyl iodide and a mixture of barium oxide with barium hydroxide octahydrate provided essentially quantitative yields of the desired dimethylated derivative both as crystals (about two-thirds of the total yield), and as additional product found in the mother liquor, which can be further pursued to increase the yield. When this reaction was carried out in a multikilogram quantity, the yield of crystals was 77%. When barium hydroxide monohydrate was used instead of barium hydroxide octahydrate, the reaction proceeded very slowly. The methyl iodide procedure provides a preferable means for attaining the product, a 4,7-di-O-methyl 8,9-isopropylidene Neu5Ac methyl ester methyl ketoside:

[4]

If silver oxide was used instead of the mixed barium bases, only the monomethylated derivative was obtained. Alternatively, the 4,7-di-O-methyl derivative could be obtained in high yield (about 75% after chromatographic purification) by reaction with dimethylsulfate in the presence of sodium hydride at low temperature.

The second principal alternative to preparing the 4,7-di-O-alkyl derivative is via the 8,9-epoxide protected intermediate. As in the first alternative, dialkylation may be attained by using an alkyl halide, preferably a higher halide such as bromide or iodide, in the presence of a basic substance. As noted above, the alkyl group may be methyl, ethyl, propyl, isopropyl, and normal or branched butyl. In a preferred embodiment of the method of the invention, the reagent employed in this reaction is methyl iodide. In this embodiment, however, the basic substance is preferably silver oxide. This combination of reagents provides yields of about 75–80% after chromatographic purification. An alternative procedure relies on reaction with dimethylsulfate in the presence of sodium hydride, and likewise provides an advantageous yield of the desired product, a 4,7-di-O-methyl 8,9-epoxide Neu5Ac methyl ester methyl ketoside:

[6]

Other reaction conditions yielded N-methylation (methyl iodide and sodium hydride) or deesterification (use of barium oxide and barium hydroxide octahydrate).

The reaction strategies yielding the 4,7-dimethyl 8,9-protected Neu5Ac methyl ester methyl ketosides described above represent a significant and unexpected improvement over the results predicted from the state of the art available at the time this invention was made. As noted in U.S. Pat. No. 5,719,020, excess alkylating agent, such as dimethylsulfate, when employed to treat the 8,9-ketal protected Neu5Ac methyl ester methyl ketoside, yields a mixture of the 4-monoalkyl and the 4,7-dialkyl derivatives. The dialkyl derivative is commonly the minor product, and may at best be brought to the level of being about equal, in molar ratio, to the monoalkyl derivative. The dialkyl derivative was not purified from the mixture in the earlier methods; rather the mixture was used directly in the subsequent steps.

The 8,9-protected 4,7-di-O-alkyl Neu5Ac methyl ester methyl ketosides are next deprotected and derivatized at the 8,9 position by acetylation. In the same set of reactions, the methyl ketoside group is also deprotected and acetylated. A series of steps is undertaken in which purification of intermediates need not be carried out, and only the product of the last step, namely, the triacetylated derivative, is purified. The product is the same whether the starting substance is protected by the isopropylidene group or by the epoxide group at the 8- and 9-positions. Specifically, in the preferred embodiment outlined herein, the product obtained in this set of reactions is a 2,8,9-triacetyl derivative of 4,7-di-O-methyl Neu5Ac methyl ester:

[7]

The deprotection of the 4,7-dialkyl derivative is carried out under alkaline conditions in aqueous alcohol. Beneficially the alcohol used corresponds to the alkyl group present at the 4- and 7-positions. The base is then neutralized with a combination of a soluble acid and the protonated form of a strong cation exchange resin. After further treatment with dilute aqueous acid, the deprotected derivative is dried and contacted with anhydrous alcohol in the presence of a strong anhydrous acid. After drying again, the 2,8,9-triacetyl derivative of 4,7-di-O-alkyl Neu5Ac methyl ester is obtained by acetylation using acetic anhydride in pyridine, in the presence of an organic base such as dimethylaminopyridine. In the case where the 4- and 7-alkyl substituents are methyl, yields of the triacetylated product are about 50–65% based on the 4,7-di-O-methyl 8,9-protected Neu5Ac methyl ester methyl ketoside.

The subsequent step specifically displaces the ketoside acetate group by chloride. Thus a 2,8,9-triacetyl derivative of 4,7-di-O-alkyl Neu5Ac methyl ester is converted into a 2-chloro-8,9-diacetyl derivative of 4,7-di-O-alkyl Neu5Ac methyl ester. This activated derivative can readily be used to generate the desired chromogenic glycoside. The conversion is readily accomplished by treating the triacetyl derivative with anhydrous HCl in the presence of acetyl chloride. Alternatively, the reaction may be carried out by treating the derivative with anhydrous HCl in dichloromethane. When the starting material is a 2,8,9-triacetyl derivative of 4,7-di-O-methyl Neu5Ac methyl ester, the step yield is high, approaching quantitative conversion. The product is:

[8]

A chromogenic ketoside of the 8,9-diacetyl derivative of 4,7-dialkyl Neu5Ac methyl ester is prepared by contacting the product of the preceding reaction, a 2-chloro-8,9-diacetyl derivative of 4,7-dialkyl Neu5Ac methyl ester, with a composition that generates a reactive form of the chromogenic moiety. In an advantageous embodiment, the reactive form includes the oxyanion derivative of the chromogenic moiety. This reactive form may then displace the 2-chloro group of the 2-chloro-8,9-diacetyl derivative of 4,7-di-O-alkyl Neu5Ac methyl ester, yielding an 8,9-diacetyl derivative of 4,7-di-O-alkyl Neu5Ac methyl ester chromogenic ketoside. In the preferred embodiment set forth above, a 4,7-di-O-methyl chromogenic ketoside in which the chromogenic moiety is the 5-bromo-3-indolyl group, has the structure:

The reaction proceeds advantageously in a variety of implementations. In one implementation, the chromogenic moiety derivatized with acetate is brought into contact with a 2-chloro-8,9-diacetyl derivative of 4,7-di-O-alkyl Neu5Ac methyl ester in the presence of strong base such as an alkali metal alkoxide in an aprotic solvent. The product obtained may subsequently be reacetylated using acetic anhydride in pyridine in a fashion similar to the acetylation described above. In another embodiment of this step, the chromogen acetate is suspended in acetone solution and aqueous sodium hydroxide is added. A 2-chloro-8,9-diacetyl derivative of 4,7-di-O-alkyl Neu5Ac methyl ester is slowly added and alkaline conditions are maintained. In yet another implementation of this step, the chromogen acetate is suspended in an aprotic organic solvent and solid potassium hydroxide is added. A 2-chloro-8,9-diacetyl derivative of 4,7-di-O-alkyl Neu5Ac methyl ester is then added. In general, an 8,9-diacetyl derivative of 4,7-di-O-alkyl Neu5Ac methyl ester chromogenic ketoside is purified in these implementations by silica gel chromatography. When the 4- and 7-alkyl groups are methyl, step yields range from about 35% to about 70%.

The 8,9-diacetyl derivative of a 4,7-di-O-alkyl Neu5Ac methyl ester chromogenic ketoside is deprotected in a single procedure by the base catalyzed cleavage of the various ester groups. For example, the ketoside may be treated first with sodium methoxide in methanol, and then, without purification, by the addition of aqueous sodium hydroxide. The desired final product, a 4,7-di-O-alkyl Neu5Ac chromogenic ketoside, is obtained, as illustrated for the preferred 4,7-di-O-methyl derivative:

[9]

It may be purified, for example, by normal phase and reversed phase chromatography of either the sodium salt form or the free acid, as appropriate. When the 4- and 7-alkyl groups are methyl, the step yield is about 75%.

The synthetic strategies yielding the 4,7-di-O-alkyl Neu5Ac chromogenic ketosides described above represent an unanticipated improvement over the results expected from the state of the art available at the time this invention was made. As noted in U.S. Pat. No. 5,719,020, methylation of the 8,9-ketal protected Neu5Ac methyl ester methyl ketoside by the reactions disclosed therein yielded a mixture of the 4-monomethyl and the 4,7-dimethyl derivatives, with the dimethyl derivative being the minor product. As practiced in U.S. Pat. No. 5,719,020, the mixture is not purified. Instead the mixed chromogenic glycosides are prepared and resolved to give the desired dialkyl derivative only at the stage of this final product. It is pointed out in U.S. Pat. No. 5,719,020 that 4-monoalkyl chromogenic glycosides of Neu5Ac are substrates for mumps neuraminidase and neuraminidases of other viruses. The patent states that the level of 4-monomethyl derivative should be less than 5%, and preferably less than 0.5%, in the purified 4,7-dimethyl product in order to provide a substrate preparation that specifically detects only influenza types A and B. That patent describes an example where in only 4 mg of highly purified 4,7-dimethylated product [9], containing less than about 5% of the 4-monomethyl derivative, was obtained from 700 mg of 2-chloro-8,9-diacetyl derivative of 4,7-dimethyl Neu5Ac methyl ester [8]. This represents a cumulative yield of less than 1% for the two steps involved, namely, formation of the chromogenic ketoside and removal of the derivatizing acetyl groups. The corresponding yield obtained using a method of the present invention is about 25% to about 50% (combining yields for the two steps disclosed in the previous two paragraphs; see also Examples 13–17). This represent s greater than a 25- to 50-fold improvement over the prior art method.

The examples which follow describe synthetic reactions involving large quantities of materials, both reactants and products, at all stages of the synthetic route. From those examples, it is apparent that the methods of the invention provide efficient, economical procedures for the preparation of 4,7-dialkyl Neu5Ac chromogenic glycosides on a commercial scale. The purity afforded is high, assuring excellent selectivity for the detection of influenza A and B viruses while distinguishing from related viruses whose virions also carry neuraminidase activity.

EXAMPLES

Example 1

Synthesis of Neu5Ac Methyl Ester Methyl Ketoside

A suspension of Neu5Ac [1] (294 g, 0.94 mol) in methanol (11.76 L, 2.5%) was treated with Bio-Rad™ (H⁺) resin (147 g) and the reaction mixture was refluxed with stirring for 72 h at 63° C. The mixture was cooled, filtered and washed with 5.0 L of methanol. The methanol was evaporated to 500 mL and the mixture kept at −10° C. overnight to crystallize the product. The filtered crystals were washed with a mixture of ethyl acetate:methanol (6:1 v/v) to provide 196 g Neu5Ac methyl ester methyl ketoside [2]. In several replicates yields ranged from 61 to 64%. In some cases the ethyl acetate:methanol washings were processed further to recover additional product.

Example 2
One-Step Synthesis of 8,9-Isopropylidene Neu5Ac Methyl Ester Methyl Ketoside p-Toluenesulfonic acid containing one molecule of water (3.73 g, pH ~1.0 as determined using pH paper (Whatman type CF, catalog no. 2613991, pH range 0–14)) was added to a solution of Neu5Ac methyl ester methyl ketoside [2] (150 g, 0.45 mol) in anhydrous acetone (2.5 L, dried over 4Å molecular sieves). The reaction mixture was stirred for 3 h at room temperature, by which time the starting material was completely consumed. The mixture was neutralized with triethylamine (4.0 mL) to reach a pH of 6–7, and the resulting mixture was evaporated to dryness. The solid mass was triturated and washed with ether to provide 150.06 g of 8,9-isopropylidene Neu5Ac methyl ester methyl ketoside [3]. The ether washings were treated in the same way to provide an additional 11.6 g of the product, giving a total of 161.6 g (96%).

Three additional batches provided comparable results. In one variation, the triethylamine was added to attain a pH of 8–9, and evaporated at 40° C. to give a thick syrup. Addition of ether provided crystals. The mother liquor was again processed to provide additional product. The overall yield was 92%.

Example 3
Synthesis of 4,7-Di-O-Methyl 8,9-Isopropylidene Neu5Ac Methyl Ester Methyl Ketoside Barium oxide (236.14 g, 1.54 mol) and barium hydroxide octahydrate (27.85 g, 0.12 mol) were added at 0° C. to a suspension of 8,9-isopropylidene Neu5Ac methyl ester methyl ketoside [3] as provided in Example 2 (161.6 g, 0.43 mol) in dry dimethylformamide (DMF, 1.3 L) over molecular sieves (161.6 g). After 10 min, methyl iodide (392.2 mL, 6.3 mol, dried over 4Å molecular sieves) was added. The mixture was stirred, maintained at room temperature, for 45 h. The solids were filtered and washed thoroughly with dichloromethane (2.0 L; five washes of 400 mL) and evaporated to dryness. The remaining syrup was washed with cold 5% HCl solution (1.0 L), then with aqueous saturated sodium bicarbonate (0.5 L), then with water (0.5 L), dried over $Na_2SO_4$, and finally dried by evaporation. The product was crystallized after dissolving in minimal dichloromethane and adding ether at 0° C. The yield of 4,7-di-O-methyl 8,9-isopropylidene Neu5Ac methyl ester methyl ketoside [4] crystals was 107.0 g (62% yield); 59 g of mother liquor containing the product, along with impurities arising from opening of the isopropylidene ring and N-methylated side product, was pursued to provide additional di-O-methylated product.

In an analogous procedure, the reaction provided a red brown syrup after filtering and removing the solvents; the syrup was diluted with 4.0 L of dichloromethane. The solids were filtered off on Celite and washed with additional dichloromethane. After evaporating off the solvent, the brown solid was dissolved in dichloromethane (12.0 L), washed with cold 2.5% HCl (4.0 L), and then with aqueous sodium thiosulfate solution (4.0 L). The aqueous washes were back extracted with dichloromethane (4.0 L). The combined organic layers were dried over anhydrous $Na_2SO_4$, and solid sodium bicarbonate was added until a slightly basic pH of 7.5, as determined using pH paper, was attained. The solution was filtered and evaporated to afford a brown syrup which was dried under vacuum for 15 h. The dried solid was crushed with ether and crystallized to afford light yellow crystals (297 g, 65%). The mother liquor (125 g) enriched in product was also processed separately without further purification in the acetylation step (see Example 4).

Example 4
Synthesis of 4. 7-Di-O-Methyl 2,8,9-Tri-O-acetyl Neu5Ac Methyl Ester 4,7-Di-O-methyl 8,9-isopropylidene Neu5Ac methyl ester methyl ketoside [4] (398 g, 0.98 mol) was suspended in a mixture of methanol and water (1:1 v/v, 3.7 L). NaOH (1.0 N, 2.05 L) was added and the reaction mixture was stirred for 2 h. The reaction was neutralized by adding Bio-Rad™ ($H^+$) resin (155 g). The resin was filtered off, washed with methanol (3.0 L) and the washing evaporated to dryness. HCl (0.03 M, 6.64 L) was added to the residue as well as Bio-Rad™ ($H^+$) resin (400 g). The resulting mixture was heated at 70° C. for 16 h. The resin was filtered off and washed with water (2.0 L). The solvent was evaporated off and the residue was dissolved in dry methanol (5.1 L). Bio-Rad™ ($H^+$) resin (347 g, dried over $P_2O_5$) was added and the reaction mixture was stirred for 5 h at room temperature. The resin was filtered off and the methanol was evaporated with the addition of pyridine (100 mL). The residue was dried under high vacuum for 15 h over $P_2O_5$. It was then treated with acetic anhydride (1.0 L), pyridine (1.0 L), and dimethylaminopyridine (30 g) for 15 h at room temperature. The liquids were evaporated off and the residue was purified by chromatography on silica gel. The column was washed with mixtures of hexane and ethyl acetate (2:1, then 1:1), and then the product was eluted with ethyl acetate. After evaporating off the ethyl acetate, 4,7-di-O-methyl 2,8,9-triacetate Neu5Ac methyl ester ketoside [7] was crystallized by dissolving it in minimal dichloromethane, adding ether and crystallizing it at −15° C. for 15 h. Crystals (364 g, 65%) were obtained after repeated crystallization. An additional yield of 10% can be obtained by reprocessing the mother liquor.

Example 5
Synthesis of 9-Tosyl Neu5Ac Methyl Ester Methyl Ketoside

Neu5Ac methyl ester methyl ketoside [2] (39.5 g, 0.12 mol) in anhydrous pyridine (140 mL) was cooled to 0° C. p-Toluenesulfonyl chloride (11.2 g, 0.059 mol) was added in small portions. The reaction continued for 1 h while the temperature was allowed to rise to 10° C. Three further portions of p-toluenesulfonyl chloride (5.6 g, 0.03 mol each) were added hourly. The starting material was consumed at that time. The reaction was quenched by adding methanol, and the solution was concentrated. The solid product, 9-tosyl Neu5Ac methyl ester methyl ketoside, was purified by chromatography on silica gel (70–230 mesh) using dichloromethane and dichloromethane:methanol (9:1) as eluent. The yield was 40.9 g (71%).

Example 6
Synthesis of Neu5Ac 8,9-Epoxide Methyl Ester Methyl Ketoside

9-Tosyl Neu5Ac methyl ester methyl ketoside (12.33 g, 25 mmol) was dissolved in methanol (120 mL) and 0.5 M sodium methoxide was added at room temperature. The reaction mixture was stirred for 20 min and evaporated to dryness. The solid material was purified by chromatography on silica gel (70–230 mesh) using dichloromethane:methanol:pyridine (90:10:0.1, and 85:15:0.1) as eluents; product was eluted in both solvents. The eluates were combined and treated to provide Neu5Ac 8,9-epoxide methyl ester methyl ketoside [5] (7.27 g, 86.5%) as a white solid.

Example 7
Synthesis of 9-Mesyl Neu5Ac Methyl Ester Methyl Ketoside

Methanesulfonyl chloride (252 µL, 1.1 eq.) was added to a solution of Neu5Ac methyl ester methyl ketoside [2] (1.0 g, 2.97 mmol) in anhydrous pyridine (5.0 mL) at –10° C. under nitrogen. The reaction mixture was stirred for 30 min., at which time the reaction was found to be complete. Excess mesyl chloride was quenched with methanol (2.0 mL) and the solvents evaporated. The 9-mesyl Neu5Ac methyl ester methyl ketoside was purified by chromatography on silica gel (70–230 mesh) using dichloromethane:methanol (95:5) as eluent. The yield was 1.10 g (81.2%).

Example 8
Direct Synthesis of Neu5Ac 8,9-Epoxide Methyl Ester Methyl Ketoside from Neu5Ac Methyl Ester Methyl Ketoside Methanesulfonyl chloride (252.5 µL, 3.26 mmol) was added dropwise to a solution of Neu5Ac methyl ester methyl ketoside [2] (1.0 g, 2.97 mmol) in anhydrous pyridine (5.0 mL) at –10° C. The mixture was stirred for 1.5 h. Methanol (5.0 mL) was added and the resulting mixture was evaporated to dryness. To the residue was added a solution of 0.5 N sodium methoxide in methanol (7.5 mL) and the mixture was stirred for 1 h at room temperature. The mixture was neutralized with Dowex-50(H+) resin to pH ~8.0 and evaporated. The residue was purified by chromatography on silica gel (70–230 mesh) using dichloromethane:methanol:pyridine (95:5:0.1 and 90:10:0.1) as eluents (both eluates contain product) to obtain Neu5Ac 8,9-epoxide methyl ester methyl ketoside [5] (605 mg, 63.8%).

In a variation of this procedure, the Neu5Ac methyl ester methyl ketoside was treated with p-toluenesulfonyl chloride, in two increments, at –20° C. Using essentially the same purification procedure as detailed above, the epoxide product was obtained in about 65% yield.

Example 9
Synthesis of 4,7-Di-O-Methyl 8,9-Epoxide Neu5Ac Methyl Ester Methyl Ketoside To a solution of Neu5Ac 8,9-epoxide methyl ester methyl ketoside [5] (500 mg, 1.57 mmol) in mixed solvent DMF:tetrahydrofuran (THF) (1:1, 4.0 mL) was added dimethyl sulfate (1.19 mL, 8.0 eq.) at –10° C., followed by sodium hydride (103.4 mg, 2.2 eq., 80% dispersion in oil) with stirring. The reaction was allowed to proceed for 45 min. Additional sodium hydride (0.4 eq.) was added and the mixture was stirred for 20 min further at –10° C. Some monomethylated product was still detected by thin layer chromatography (TLC). After 30 min, the reaction was quenched with methanol (1.0 mL) and the mixture was evaporated. The residue was diluted with dichloromethane (150 mL), washed with water (50 mL), dried over anhydrous sodium sulfate, filtered, and evaporated. The crude mass was purified by chromatography on silica gel using dichloromethane:methanol:-pyridine (98:2:0.1 and 95:5:0.1) as eluents (both eluates contain product) to provide 4,7-di-O-methyl 8,9-epoxide Neu5Ac methyl ester methyl ketoside [6] (370 mg, 68.1%).

In a second experiment, the same procedure was used except that a second supplement of sodium hydride was added (0.2 eq.) and allowed to react for 0.5 hr. The final yield in this case remained at 68%.

Example 10
Synthesis of 4,7-Di-O-Methyl 8,9-Epoxide Neu5Ac Methyl Ester Methyl Ketoside To a solution of Neu5Ac 8,9-epoxide methyl ester methyl ketoside [5] (5.5 g, 17.2 mmol) in mixed DMF:toluene (9:1, 50 mL), was added methyl iodide (6.4 mL, 103.33 mmol), followed by freshly prepared solid silver oxide (12 g, 51.6 mmol). The mixture was stirred at 50° C. for 15 h, by which time all the starting material was consumed. The reaction mixture was diluted with dichloromethane (250 mL) and evaporated to dryness. The residue was purified by chromatography on silica gel using dichloromethane:methanol:pyridine (98:2:0.1 and 95:5:0.1) as eluents (both eluates contain product) to provide 4,7-di-O-methyl 8,9-epoxide Neu5Ac methyl ester methyl ketoside [6] (4.5 g, 75.2%).

Example 11
Synthesis of 4,7-Di-O-Methyl 2,8,9-Tri-O-acetyl Neu5Ac Methyl Ester 4,7-Di-O-methyl 8,9-epoxide Neu5Ac methyl ester methyl ketoside [6] (3.0 g, 8.23 mmol) was dissolved in methanol (30 mL) and a solution of 1.0 M sodium hydroxide (15 mL) was added. The reaction mixture was stirred for 1 h. TLC indicated the reaction was complete. The mixture was neutralized with Dowex-50 (H+) resin to pH ~7 as determined using pH paper, filtered, the resin washed with methanol, and the combined solution was evaporated.

The residue was suspended in 0.025 M HCl and Dowex-50 (H+) resin (3.0 g) was added. The mixture was heated for 40 min at 100° C. The mixture was filtered and the resin was washed with methanol. The combined solvent was removed to provide the crude hydrolysis product.

The hydrolysate was dissolved in dry methanol (40 mL) and trifluoroacetic acid (0.6 mL) was added. The mixture was stirred for 4.5 h at 65° C. The solvent was removed and the residue was dried under high vacuum.

To the methylated residue was added acetic anhydride (9 mL), pyridine (20 mL) and dimethylaminopyridine (0.2 g), and the acetylation was allowed to proceed for 15 h. Solvents were evaporated and the residue was purified by chromatography on silica gel (230–400 mesh) using dichloromethane:methanol:-pyridine (98:2:0.1) as eluent to obtain 4,7-di-O-methyl 2,8,9-tri-acetyl Neu5Ac methyl ester [7] (1.93 g, 49%).

Example 12
Synthesis of 2-Chloro 4,7-Di-O-methyl 8,9-Di-O-acetyl Neu5Ac Methyl Ester 4,7-Di-O-methyl 2,8,9-tri-O-acetyl Neu5Ac methyl ester [7] (56.0 g, 0.12 mol) in anhydrous dichloromethane (1.0 L) was treated with acetyl chloride (56.0 mL) at 0° C. with a steady stream of anhydrous HCl for 3 h. At this time none of the starting material remained. The solvent was evaporated, and further added toluene was evaporated (500 mL, 3×x). The residue was dried under high vacuum for 1 h. The 2-chloro 4,7-di-O-methyl 8,9-diacetate Neu5Ac methyl ester [8] was dissolved in DMF:THF (1:1, 220 mL) and dried over 4Å molecular sieves (28.0 g). It was used directly without further purification in the synthesis of the chromogenic ketoside.

Example 13
Synthesis of 5-Bromo-3-Indolyl 4,7-Di-O-Methyl 8,9-Di-O-acetyl Neu5Ac Methyl Ester Ketoside 5-Bromo-3-indolyl acetate (46.23 g, 0.18 mol) was dissolved in mixed DMF:THF (1:1, v/v, 200 mL) at room temperature. The solution was cooled at −10° C. for 20 min and potassium tert-butoxide (20.43 g, 1.5 eq.) was added. The crude, dried, 2-chloro 4,7-di-O-methyl 8,9-diacetate Neu5Ac methyl ester [8] dissolved in DMF:THF (1:1, 220 mL) from Example 12 was added to the reaction mixture dropwise at −10° C., and stirred for 15 h at this temperature. Thin layer chromatography (TLC) showed only the desired ketoside. The mixture was diluted with dichloromethane (2.0 L) and washed with water (250 mL). The aqueous wash was back extracted with dichloromethane (4×500 mL), and the combined organic solutions were evaporated, then coevaporated with toluene (3×500 mL) to dryness under high vacuum. The residue was treated with acetic anhydride (500 mL) and pyridine (500 mL) for 15 h at room temperature. The solution was evaporated, then coevaporated with toluene (3×500 mL). The residue was purified by chromatography on silica gel (230–400 mesh) using toluene:acetone (9:1, 5:1, 3:1) as eluents (the product occurred in the latter two eluates) to provide 5-bromo-3-indolyl 4,7-di-O-methyl 8,9-di-O-acetyl Neu5Ac methyl ester ketoside (55.0 g, 70%). The product was crystallized from a mixture of dichloromethane and ether to give 45.0 g (57.3% yield) crystalline product. 10.0 g of the mother liquor, containing additional product and the elimination side product, was treated separately for deprotection in succeeding steps.

In a second example of this reaction, the product was purified by chromatography on Iatrobeads (Iatron Laboratories, Inc., Tokyo, Japan) using toluene:acetone (5:1, 3:1) as eluents (both eluates contain product) to provide 54.0 g of the product (75%), which was crystallized from a mixture of dichloromethane and ether to give 40.0 g of crystalline material. 14.0 g of the mother liquor, containing additional product and the elimination side product, was treated separately for deprotection in further steps.

Example 14
Synthesis of 5-Bromo-3-Indolyl 4,7-Di-O-Methyl 8,9-Di-O-acetyl Neu5Ac Methyl Ester Ketoside 5-Bromo-3-indolyl acetate (130 mg, 0.512 mmol) was suspended in acetone (3.0 mL) and 1.0 M NaOH (0.54 mL) was added dropwise. The mixture became clear green with a pH of ~7–8 as determined using pH paper. The solution was cooled to 0° C. and 2-chloro 4,7-di-O-methyl 8,9-diacetyl Neu5Ac methyl ester [8] from Example 12 dissolved in acetone (3.0 mL) was added slowly. The color of the solution slowly turned to yellowish-brown. After 30 min, TLC indicated that the reaction was not complete; the pH of the reaction mixture was ~5–6. Another aliquot of 1.0 M NaOH (0.5 mL) was added. The solution became green again and was stirred for 1 h more at 0° C., and then was allowed to stir at room temperature for 30 min. TLC indicated the reaction was complete, with the pH being ~6–7. The solvent was removed and the residue was chromatographed on silica gel (230–400 mesh) using dichloromethane:methanol (20:1) as eluent to provide a light brown solid, 5-bromo-3-indolyl 4,7-di-O-methyl 8,9-di-O-acetyl Neu5Ac methyl ester ketoside (110.0 mg, 38.0% based on the two steps beginning at Example 12).

In a second example of this step, the reaction was run at room temperature, and it was found that a second supplement of NaOH was required. The yield, based on two steps, was 40%.

Example 15
Synthesis of 5-Bromo-3-Indolyl 4,7-Di-O-Methyl 8,9-Di-O-acetyl Neu5Ac Methyl Ester Ketoside 5-Bromo-3-indolyl acetate (156 mg, 0.61 mmol) was dissolved in mixed DMF:THF (1:1, v/v, 200 mL) at room temperature. The solution was cooled at 0° C. for 20 min, and solid potassium hydroxide (40.0 mg, 1.65 eq.) was added. 2-Chloro 4,7-di-O-methyl 8,9-diacetate Neu5Ac methyl ester [8] from Example 12 dissolved in mixed DMF:THF (1:1 v/v, 2.0 mL) was added dropwise at 0° C. After stirring for 15 h at 0° C., TLC showed only the ketoside product The reaction mixture was diluted with dichloromethane (150 mL) and washed with water (30 mL). The aqueous wash was back extracted with dichloromethane (3×50 mL), and the combined dichloromethane solutions were dried over anhydrous sodium sulfate, filtered, and evaporated to dryness under high vacuum. The residue was chromatographed on silica gel (230–400 mesh) using toluene:acetone (9:1, 5:1, 3:1) as eluents, with product found in the latter two eluents, to provide 5-bromo-3-indolyl 4,7-di-O-methyl 8,9-di-O-acetyl Neu5Ac methyl ester ketoside (150 mg, 55% based on the two steps beginning at Example 12).

Example 16
Synthesis of 5-Bromo-3-Indolyl 4,7-Di-O-Methyl Neu5Ac Ketoside

5-Bromo-3-indolyl 4,7-di-O-methyl 8,9-di-O-acetyl Neu5Ac methyl ester ketoside (45.0 g, 0.067 mol) was dissolved in sodium methoxide in methanol (150 mL) and stirred for 1 h at room temperature. 1.0 M NaOH (150 mL) was added and the mixture was stirred for 1 h. The solution was neutralized with Bio-Rad (H⁺) resin to give a pH of 8–9 as determined by pH paper. The resin was filtered off, and the filtrate was evaporated to dryness. The residue was purified by chromatography on silica gel (70–230 mesh) using dichloromethane and dichloromethane:methanol:water:pyridine (80:20:1:1) as eluent to provide the free acid 5-bromo-3-indolyl 4,7-di-O-methyl Neu5Ac ketoside which was converted into the sodium salt [9] by passage through Bio-Rad AG-50W-X-8 (Na⁺) ion exchange resin. The sodium salt was lyophilized. The result was applied to a C-18 reverse phase column and washed with water, followed by 5% acetonitrile-water solution. The colorless fractions containing the product were pooled and evaporated under high vacuum at 30° C. to a volume of 500 mL which was lyophilized to provide the final product (27.5 g, 74.2%). Mother liquor from the previous step was processed separately, providing additional final product.

In further examples of this procedure, the yields were 76.8% and 66%.

Example 17
Direct Synthesis of 5-Bromo-3-Indolyl 4,7-Di-O-Methyl Neu5Ac Ketoside from 2-Chloro 4,7-Di-O-methyl 8,9-Di-O-acetyl Neu5Ac Methyl Ester 5-Bromo-3-indolyl acetate (1.13 g, 4.18 mmol) was dissolved in DMF (3.0 mL) and potassium tert-butoxide (446 mg, 3.97 mmol) was added. The solution was stirred for 10 min and cooled to 0° C. for 20 min. The crude, dried, 2-chloro-4,7-di-O-methyl 8,9-diacetate Neu5Ac methyl ester [8] from Example 12 dissolved in anhydrous tetrahydrofuran (10.0 mL) was added to the reaction mixture dropwise. The reaction continued for 90 min while the temperature rose to room temperature. TLC showed that the starting material disappeared and a new spot appeared. The mixture was diluted with methanol (20.0 mL) and a solution of 2 N sodium methoxide in methanol was added to adjust the pH to ~9–10 as determined using pH paper. After 30 min, water (10.0 mL) was added and allowed to react for 2 h to hydrolyze the ester. TLC showed that the reaction was complete. The reaction mixture was neutralized with Amberlite IR-120 ($H^+$) to pH ~7 and the resin removed by filtration. After evaporating the reaction mixture to dryness, the crude product was loaded onto a silica gel column and eluted with methanol:dichloromethane (2:8), followed by methanol:dichloromethane:water (20:80:2). The latter eluate containing the product was collected and evaporated to provide a slightly colored residue. The solid was dissolved in methanol and converted to the sodium salt by the addition of saturated aqueous sodium bicarbonate. The solution was evaporated to dryness, dissolved in water, and applied to a C-18 reverse phase column. The column was eluted with water, then with methanol:water (10:90). The fractions containing the product were collected, concentrated, and lyophilized to provide the sodium salt of 5-bromo-3-indolyl 4,7-di-O-methyl Neu5Ac ketoside [9] (530 mg, 47% based on the three steps from Example 12).

The synthetic procedures exemplified above provide overall yields, starting from Neu5Ac and ending with the sodium salt of 5-bromo-3-indolyl 4,7-di-O-methyl Neu5Ac ketoside that range from about 10% to about 15%. The yield depends on which synthetic route is followed from among the choices outlined in this specification and the Examples. The best overall yield may be obtained using the isopropylidene protection, followed by O-methylation in the presence of barium oxide/barium hydroxide, and glycosylation using potassium tert-butoxide as the activator. The cumulative yields obtainable following the procedures outlined in the present invention are far greater than that which the state of the prior art would predict.

The disclosure of U.S. Pat. No. 5,719,020 demonstrates that 5-bromo-3-indolyl 4,7-di-O-methyl Neu5Ac ketoside is selectively susceptible to enzymatic cleavage by only influenza neuraminidase, while remaining refractory to the action of neuraminidase activities found on other virus species that were tested.

We claim:

1. A method of preparing a 4,7-di-O-alkyl chromogenic ketoside of N-acetylneuraminic acid (Neu5Ac), said method comprising, in order, the following steps:
    (a) alkylating Neu5Ac on the C1 carboxyl and C2 (anomeric) hydroxyl to provide an alkyl ester alkyl ketoside derivative of Neu5Ac;
    (b) protecting the 8- and 9-hydroxyl groups of the alkyl ester alkyl ketoside derivative of Neu5Ac to form a protected alkyl ester alkyl ketoside derivative of Neu5Ac;
    (c) alkylating the 4- and 7-hydroxyl groups of the protected alkyl ester alkyl ketoside derivative of Neu5Ac by contacting the derivative with an alkyl halide to form a 4,7-di-O-alkyl protected alkyl ester alkyl ketoside derivative of Neu5Ac;
    (d) selectively deprotecting the 8- and 9-hydroxyl groups and dealkylating the 2-hydroxyl group of the ketoside product obtained in step (c) and derivatizing the resulting 2-, 8-, and 9-hydroxyl groups;
    (e) activating the anomeric carbon of the product obtained in step (d) to form a 4,7-di-O-alkyl alkyl ester derivative of Neu5Ac, derivatized at the 8- and 9-hydroxyls, and activated at the anomeric carbon;
    (f) contacting the product obtained in step (e) with a suspension of a chromogenic moiety in a solvent to form a chromogenic ketoside of a 4,7-di-O-alkyl alkyl ester derivative of Neu5Ac, derivatized at the 8- and 9-hydroxyls; and
    (g) obtaining a 4,7-di-O-alkyl chromogenic ketoside of Neu5Ac from the derivatized chromogenic ketoside obtained in step (f).

2. The process described in claim 1 wherein protecting the 8- and 9-hydroxyl groups described in step (b) comprises forming a ketal.

3. The process described in claim 2 wherein ketal is formed using an acid catalyst chosen from the group consisting of p-toluenesulfonic acid, a salt of p-toluenesulfonic acid, $ZnCl_2$, and $FeCl_3$.

4. A process of preparing a 4,7-di-O-alkyl chromogenic ketoside of N-acetylneuraminic acid (Neu5Ac), said method comprising, in order, the following steps:
    (a) alkylating Neu5Ac on the C1 carboxyl and C2 (anomeric) hydroxyl to provide an alkyl ester alkyl ketoside derivative of Neu5Ac;
    (b) protecting the 8- and 9-hydroxyl groups of the alkyl ester alkyl ketoside derivative of Neu5Ac to form a protected alkyl ester alkyl ketoside derivative of Neu5Ac, wherein protecting the 8- and 9-hydroxyl groups comprises dehydration to form an 8,9-epoxide;
    (c) alkylating the 4- and 7-hydroxyl groups of the protected alkyl ester alkyl ketoside derivative of Neu5Ac by contacting the derivative with an alkyl halide to form a 4,7-di-O-alkyl protected alkyl ester alkyl ketoside derivative of Neu5Ac;
    (d) selectively deprotecting the 8- and 9-hydroxyl groups and dealkylating the 2-hydroxyl group of the ketoside product obtained in step (c) and derivatizing the resulting 2-, 8-, and 9-hydroxyl groups;
    (e) activating the anomeric carbon of the product obtained in step (d) to form a 4,7-di-O-alkyl alkyl ester derivative of Neu5Ac, derivatized at the 8- and 9-hydroxyls, and activated at the anomeric carbon;
    (f) contacting the product obtained in step (e) with a suspension of a chromogenic moiety in a solvent to form a chromogenic ketoside of a 4,7-di-O-alkyl alkyl ester derivative of Neu5Ac, derivatized at the 8- and 9-hydroxyls; and
    (g) obtaining a 4,7-di-O-alkyl chromogenic ketoside of Neu5Ac from the derivatized chromogenic ketoside obtained in step (f).

5. The process described in claim 1 wherein the alkyl halide employed in step (c) is methyl iodide and the composition further comprises either silver oxide or a mixture of barium oxide and barium hydroxide.

6. The process described in claim 1 wherein the derivative activated at the anomeric carbon described in step (e) has been activated by a process that comprises placing a halo substituent on the anomeric carbon.

7. The process described in claim 6 wherein the halo substituent is chloro.

8. The process described in claim 1 wherein the chromogenic moiety described in step (f) is chosen from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3- indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl, a moiety that becomes phosphorescent upon being cleaved from the ketoside, and a moiety that becomes chemiluminescent upon being cleaved from the ketoside.

9. The process described in claim 8 wherein the chromogenic moiety is 5-bromo-3-indolyl.

10. The process described in claim 1 wherein the suspension described in step (f) further comprises a base.

11. The process described in claim 10 wherein the base is chosen from the group consisting of sodium hydroxide, an alkali metal alkoxide, and a mixture of barium oxide and barium hydroxide.

12. The process described in claim 1 wherein the alkyl group on the C1 carboxyl and the alkyl group on the anomeric hydroxyl of the ketoside derivative of Neu5Ac described in step (a) are the same or different and are chosen from the group consisting of methyl, ethyl, propyl, isopropyl, and normal or branched butyl.

13. The process described in claim 12 wherein the alkyl group on the C1 carboxyl and the alkyl group on the anomeric hydroxyl are methyl.

14. The method of claim 1, wherein the alkylating of Neu5Ac on the C1 carboxyl and C2 (anomeric) hydroxyl is carried out by contacting Neu5Ac with an alkyl alcohol and a pronated form of a cation exchange resin.

15. The method of claim 1, wherein the alkylating of Neu5Ac on the C1 carboxyl and C2 (anomeric) hydroxyl is carried out by contacting Neu5Ac with an alkyl alcohol and a pronated form of a strong acid cation exchange resin.

16. The process of claim 5, wherein the composition contains the mixture of barium oxide and barium hydroxide and wherein the barium hydroxide is barium hydroxide octahydrate.

17. A method of preparing a 4,7-di-O-alkyl chromogenic ketoside of Neu5Ac comprising, in order, the following steps:
(a) alkylating Neu5Ac on the C1 carboxyl and C2 hydroxyl to provide an alkyl ester alkyl ketoside derivative of Neu5Ac;
(b) protecting the 8- and 9-hydroxyl groups of the alkyl ester alkyl ketoside derivative of Neu5Ac by forming an 8,9-epoxide protected alkyl ester alkyl ketoside derivative of Neu5Ac;
(c) alkylating the 4- and 7-hydroxyl groups of the epoxide protected alkyl ester alkyl ketoside derivative of Neu5Ac to form a 4,7-di-O-alkyl epoxide protected alkyl ester alkyl ketoside derivative of Neu5Ac;
(d) selectively deprotecting the 8- and 9-hydroxyl groups and dealkylating the 2-hydroxyl group of the ketoside product obtained in step (c) and derivatizing the resulting 2-, 8-, and 9-hydroxyl groups;
(e) activating the anomeric carbon of the product obtained in step (d) to form a 4,7-di-O-alkyl alkyl ester derivative of Neu5Ac, derivatized at the 8- and 9-hydroxyls, and activated at the anomeric carbon;
(f) contacting the product obtained in step (e) with a suspension of a chromogenic moiety in a solvent to form a chromogenic ketoside of a 4,7-di-O-alkyl alkyl ester derivative of Neu5Ac, derivatized at the 8- and 9-hydroxyls; and
(g) obtaining a 4,7-di-O-alkyl chromogenic ketoside of Neu5Ac from the derivatized chromogenic ketoside obtained in step (f).

18. The process described in claim 17 wherein the alkylating described in step (c) comprises contacting the derivative with an alkyl halide to form a 4,7-di-O-alkyl epoxide protected alkyl ester alkyl ketoside derivative of Neu5Ac.

19. The process described in claim 17 wherein the alkyl halide employed in step (c) is methyl iodide and the composition further comprises either silver oxide or a mixture of barium oxide and barium hydroxide.

20. The process described in claim 17 wherein the derivative activated at the anomeric carbon described in step (e) has been activated by a process that comprises placing a halo substituent on the anomeric carbon.

21. The process described in claim 20 wherein the halo substituent is chloro.

22. The process described in claim 17 wherein the chromogenic moiety described in step (f) is chosen from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, and 6-bromo-2-naphthyl, a moiety that becomes phosphorescent upon being cleaved from the ketoside, and a moiety that becomes chemiluminescent upon being cleaved from the ketoside.

23. The process described in claim 17 wherein the suspension described in step (f) further comprises a base.

24. The process described in claim 17 wherein the alkyl group on the C1 carboxyl and the alkyl group on the anomeric hydroxyl of the ketoside derivative of Neu5Ac described in step (a) are the same or different and are chosen from the group consisting of methyl, ethyl, propyl, isopropyl, and normal or branched butyl.

25. The process described in claim 22 wherein the chromogenic moiety is 5-bromo-3-indolyl.

26. The process described in claim 23 wherein the base is chosen from the group consisting of sodium hydoxide, an alkali metal alkoxide, and a mixture of barium oxide and barium hydoxide.

27. The process described in claim 24 wherein the alkyl group on the C1 carboxyl and the alkyl group on the anomeric hydroxyl are methyl.

28. A method of preparing a 4,7-di-O-methyl chromogenic ketoside of N-acetylneuraminic acid (Neu5Ac), said method comprising, in order, the following steps:
(a) contacting Neu5Ac with methanol and the protonated form of a cation exchange resin to methylate the C1 carboxyl group and the C2 hydroxyl group, forming a methyl ester methyl ketoside of Neu5Ac;
(b) contacting the methylated ester ketoside of Neu5Ac provided in step (a) with acetone and p-toluenesulfonic acid, to form a 8,9-isopropylidene methyl ester methyl ketoside of Neu5Ac;
(c) contacting the 8,9-isopropylidene methylated ester ketoside of Neu5Ac provided in step (b) with methyl iodide and a mixture of barium oxide and barium hydroxide to form a 4,7-di-O-methyl 8,9-isopropylidene methylated ester ketoside of Neu5Ac;
(d) selectively removing the 8,9-isopropylidene and C2 methyl groups from the ketoside product obtained in step (c) and acetylating the resulting anomeric, 8- and 9-hydroxyl groups;
(e) activating the anomeric carbon of the product obtained in step (d) by converting the acetate to chloride;
(f) contacting the activated chloride product provided in step (e) with a suspension of a derivative of 5-bromo-3-indolol and potassium tert-butoxide in a solvent to form a chromogenic ketoside of a 4,7-di-O-methyl methyl ester of Neu5Ac, acetylated at the 8- and 9-hydroxyls; and (g) deblocking the acetyl groups at the 8- and 9-hydroxyl groups and the methyl ester from the chromogenic ketoside of Neu5Ac obtained in step (f), to form the 4,7-di-O-methyl chromogenic ketoside of Neu5Ac.

29. The process of claim 25, wherein the barium hydroxide is barium hydroxide octahydrate.

30. A method of preparing a 4,7-di-O-methyl chromogenic ketoside of N-acetylneuraminic acid (Neu5Ac), said method comprising, in order, the following steps:

(a) contacting Neu5Ac with methanol and the protonated form of a cation exchange resin to methylate the C1 carboxyl group and the C2 hydroxyl group, forming a methyl ester methyl ketoside of Neu5Ac;

(b) contacting the methylated ester ketoside of Neu5Ac provided in step (a) with
  (i) an acid chloride of an organic sulfonic acid, and
  (ii) treating the result obtained in step (b)(i) with a composition containing sodium methoxide and methanol, providing an 8,9-epoxide methyl ester methyl ketoside of Neu5Ac;

(c) methylating the 4- and 7-hydroxyl groups of the 8,9-epoxide methylated ester ketoside of Neu5Ac provided in step (b) by a process chosen from the group consisting of
  (i) contacting the epoxide ketoside with a composition containing methyl iodide and silver oxide,
  (ii) contacting the epoxide ketoside with a composition containing dimethylsulfate and sodium hydride, and
  (iii) a sequential combination of step (c)(i) and step (c)(ii), providing a 4,7-di-O-methyl 8,9-epoxide methylated ester ketoside of Neu5Ac;

(d) selectively removing the 8,9-epoxide and C2 methyl groups of the ketoside product obtained in step (c) and acetylating the resulting anomeric, 8- and 9-hydroxyl groups;

(e) activating the anomeric carbon of the product obtained in step (d) by converting the acetate to chloride;

(f) contacting the activated chloride product provided in step (e) with a suspension of a derivative of 5-bromo-3-indolol and potassium tert-butoxide in a solvent to form a chromogenic ketoside of a 4,7-di-O-methyl methyl ester of Neu5Ac, acetylated at the 8- and 9-hydroxyls; and (g) deblocking the acetyl groups at the 8- and 9-hydroxyl groups and the methyl ester from the chromogenic ketoside of Neu5Ac obtained in step (f), to form the 4,7-di-O-methyl chromogenic ketoside of Neu5Ac.

* * * * *

UNITED STATES PATENT AND TRADEMARK OFFICE
CERTIFICATE OF CORRECTION

PATENT NO. : 6,303,764 B1
DATED : October 16, 2001
INVENTOR(S) : Srivastava et al.

It is certified that error appears in the above-identified patent and that said Letters Patent is hereby corrected as shown below:

<u>Title page,</u>
Item [73], Assignees, delete "Palladin Opportunity Fund, LLC; Halifex Fund, L.P., both of Maplewood, NJ (US)"

<u>Column 23,</u>
Line 5, change "25" to -- 28 --

Signed and Sealed this

Tenth Day of September, 2002

*Attest:*

JAMES E. ROGAN
*Attesting Officer*     *Director of the United States Patent and Trademark Office*